(12) United States Patent
Mohun et al.

(10) Patent No.: US 6,992,760 B2
(45) Date of Patent: Jan. 31, 2006

(54) APPARATUS AND METHOD FOR IMAGING A HISTOLOGICAL SAMPLE

(75) Inventors: Timothy J. Mohun, London (GB); Wolfgang Johann Weninger, Vienna (AT)

(73) Assignee: Medical Research Council, London (GB)

( * ) Notice: Subject to any disclaimer, the term of this patent is extended or adjusted under 35 U.S.C. 154(b) by 203 days.

(21) Appl. No.: 10/433,870

(22) PCT Filed: Dec. 11, 2001

(86) PCT No.: PCT/GB01/05432

§ 371 (c)(1),
(2), (4) Date: Jun. 4, 2003

(87) PCT Pub. No.: WO02/48692

PCT Pub. Date: Jun. 20, 2002

(65) Prior Publication Data

US 2004/0026630 A1 Feb. 12, 2004

(30) Foreign Application Priority Data

Dec. 13, 2000 (GB) .......................................... 0030310

(51) Int. Cl.
*G01N 21/64* (2006.01)

(52) U.S. Cl. ..................... 356/317; 356/36; 250/459.1; 435/40.52

(58) Field of Classification Search ................... 356/36, 356/317–318, 417; 250/458.1, 461.2; 422/82.07–82.08; 436/172; 435/40.52
See application file for complete search history.

(56) References Cited

U.S. PATENT DOCUMENTS

| 4,497,792 | A | * | 2/1985 | Gindler | .................... 435/40.52 |
| 4,960,330 | A | * | 10/1990 | Kerschmann | ................ 356/36 |
| 5,682,244 | A | * | 10/1997 | Barlow et al. | ............. 356/417 |
| 6,372,512 | B1 | * | 4/2002 | Kerschmann | ............... 436/172 |

* cited by examiner

*Primary Examiner*—F. L. Evans
*Assistant Examiner*—Kara Geisel
(74) *Attorney, Agent, or Firm*—Barnes & Thornburg

(57) ABSTRACT

A method of imaging a histological sample is provided which comprises stimulating autofluorescence in a sample using electromagnetic radiation of wavelength 750 nm. Detection of the autofluorescence is undertaken by a CCD camera, typically with an excitation filter of 510 nm disposed between the camera and the sample. The weak signal from autofluorescence is reinforced by manipulation of data acquired by the camera. Autofluorescence is detected from an upper face of the sample, an upper layer of the sample removed and a next face of the sample imaged. These steps are repeated to obtain information on autofluorescence throughout the sample. The method enables detection of features for virtually any thickness of slice, and in particular slices can range from 50 $\mu$m to 1 $\mu$m, with the method generally being used to analyse slices of thickness 5–1 $\mu$m. There is also provided a method of preparing a histological sample for use in the above method, and apparatus (10) for imaging autofluorescence in histological samples.

8 Claims, 5 Drawing Sheets

APPARATUS AND METHOD FOR IMAGING A HISTOLOGICAL SAMPLE

FIELD OF THE INVENTION

This invention relates to a method for imaging a histological sample, associated apparatus and also an associated method of preparing histological samples.

BACKGROUND TO THE INVENTION

Imaging of histological samples is generally undertaken on sections or slices of sample that have been mounted on slides and then stained to reveal features within each sample slice. However distortion of the slices occurs, for example due to shrinkage, causing a degree of misalignment between successive slices and complicating analysis of the features within the sample.

Fiducial markers have been introduced into the sample prior to sectioning so that the distortion can be compensated for. However the sample preparation and subsequent image analysis is very time consuming and difficult to automate.

An episcopic imaging method using bright field illumination and surface staining has been used to reveal tissue structure of a sample, with the uppermost surface of the sample being imaged as successive sections are in turn cut and removed. By imaging the upper surface of the sample for around $1/100^{th}$ second before removing a thin slice to reveal the next surface of the sample, distortion effects between the different images are avoided. However the resolution of features within the sample tissue is limited due to penetration of the stain, as the depth of penetration of the stain restricts how thinly the sample can be sliced.

It is an aim of the present invention to provide a method and related apparatus for imaging a histological sample that allows improved resolution of features within the sample.

SUMMARY OF THE INVENTION

According to one aspect of the present invention, there is provided a method of imaging a histological sample comprising stimulating autofluorescence in a sample and detecting autofluorescence in the sample, wherein the sample is embedded in a wax medium with stearic acid around 3 weight per cent, the wax medium incorporating a dye to suppress autofluorescence from below an upper surface of the sample, thereby to image features within the sample. Autofluorescence is the intrinsic fluorescence of a sample, and is an intrinsic property of the sample which under appropriate conditions can be stimulated to produce a weak intensity electromagnetic radiation. By using appropriate electromagnetic radiation sources and detectors, it is possible to view this weak background radiation and to use it to determine information about the structure of the sample.

The stimulation of autofluorescence may be achieved by illuminating a sample surface with electromagnetic radiation in the range 400–750 nm, preferably of wavelength 470 nm. This may be achieved by using an excitation filter of 470 nm wavelength in combination with a broadband electromagnetic radiation source.

The method may further comprise detecting electromagnetic radiation produced by autofluorescence for a period of time. Thus the detection of the autofluorescence will generally be undertaken by a CCD camera, typically with an excitation filter of 510 nm disposed between the camera and the sample, such that the camera records a large number of data sets over the period of time and obtains a large amount of data relating to autofluorescent radiation in the sample surface. The weak signal from autofluorescence can then be reinforced by manipulation of data acquired by the camera.

The method may thus further comprise recording data relating to autofluorescence in a sample for subsequent analysis and manipulation to provide information on features within a sample.

This data can be analysed and manipulated in a number of ways, for example by filtering, contrast enhancement, transforming to a grey-scale image. Movie generation of successive images is also possible by using simple programmes such as Quick Time, Movie Maker, Picts to Movie, to run a sequence of views one after the other. 3-D analysis and 3-D reconstruction may also be undertaken.

The method may also comprise staining the sample, thereby to allow detection of specific staining patterns of particular cells or tissues within the sample in combination with obtaining an image of overall histological structure through detecting autofluorescence.

The method may further comprise detecting autofluorescence from an upper face of the sample, removing an upper layer of the sample and imaging a next face of the sample, and repeating these steps thereby to obtain information on autofluorescence throughout the sample. The method enables detection of features for virtually any thickness of slice, and in particular slices can range from 50 $\mu$m to 1 $\mu$m, with the method generally being used to analyse slices of thickness 5–1 $\mu$m.

In accordance with another aspect of the invention, there is also provided a method of preparing a histological sample for use in the above method, the method of preparing the sample comprising embedding the sample in a wax medium with stearic acid of around 3 weight per cent, the wax medium incorporating a dye to supress autofluorescence from below an upper surface of the sample. By using an increased percentage of stearic acid and replacing most of the wax with Vybar, the chosen wax medium is more rigid than is usual for histological samples embedded in wax and as such is able to be sliced into thin sections of around 1–2 $\mu$m. An example of a composition of wax medium in accordance with the invention is a wax medium comprising 73% Vybar, 24% paraffin wax, and 3% stearic acid containing 0.1% red aniline wax dye as supplied by Candlemakers Supplies London.

The particular dye used allows for good surface autofluorescence at around 470/510 nm. However where other wavelengths are used to induce autofluorescence, an alternative dye may be chosen to supreas autofluorescence.

Another aspect of the invention lies in apparatus used for imaging autofluorescence in histological samples, the apparatus comprising a source of electromagnetic radiation adapted to stimulate autofluorescence in a sample, and a receiving means for receiving autofluorescent electromagnetic radiation emitted from a sample, thereby to stimulate and detect autofluorescence in a sample.

Preferably the source of electromagnetic radiation produces radiation having a wavelength of around 470 nm. The source may be provided by a pair of microscope lamps coupled to an input end of a fibre optic cable, an output end of the fibre optic cable having an excitation filter placed thereover so as to produce a wavelength of 470 nm.

The receiver means may comprise a CCD camera in combination with an emission filter, the emission filter being placed over an input face to the CCD camera. Typically the emission filter is chosen to filter out wavelengths other than 510 nm.

The CCD camera may be used with conventional software packages and data processing techniques to capture and analyse digital data relating to histological samples.

The apparatus may further comprise a sample mounting means for mounting a sample thereon, and a cutting means for thinly slicing the sample. This allows an upper face of the sample to be examined, before slicing the upper face off to reveal to a next lower face for imaging. By slicing in this way throughout the sample so as to obtain a profile of the autofluorescence throughout the sample.

Preferably the elements comprising the apparatus are in electrical communication with one another, so as to allow automation of the apparatus. This allows for automated examination of an entire sample.

The invention will now be described, by way of example, with reference to the accompanying drawings, in which.

DESCRIPTION

Figure 1:
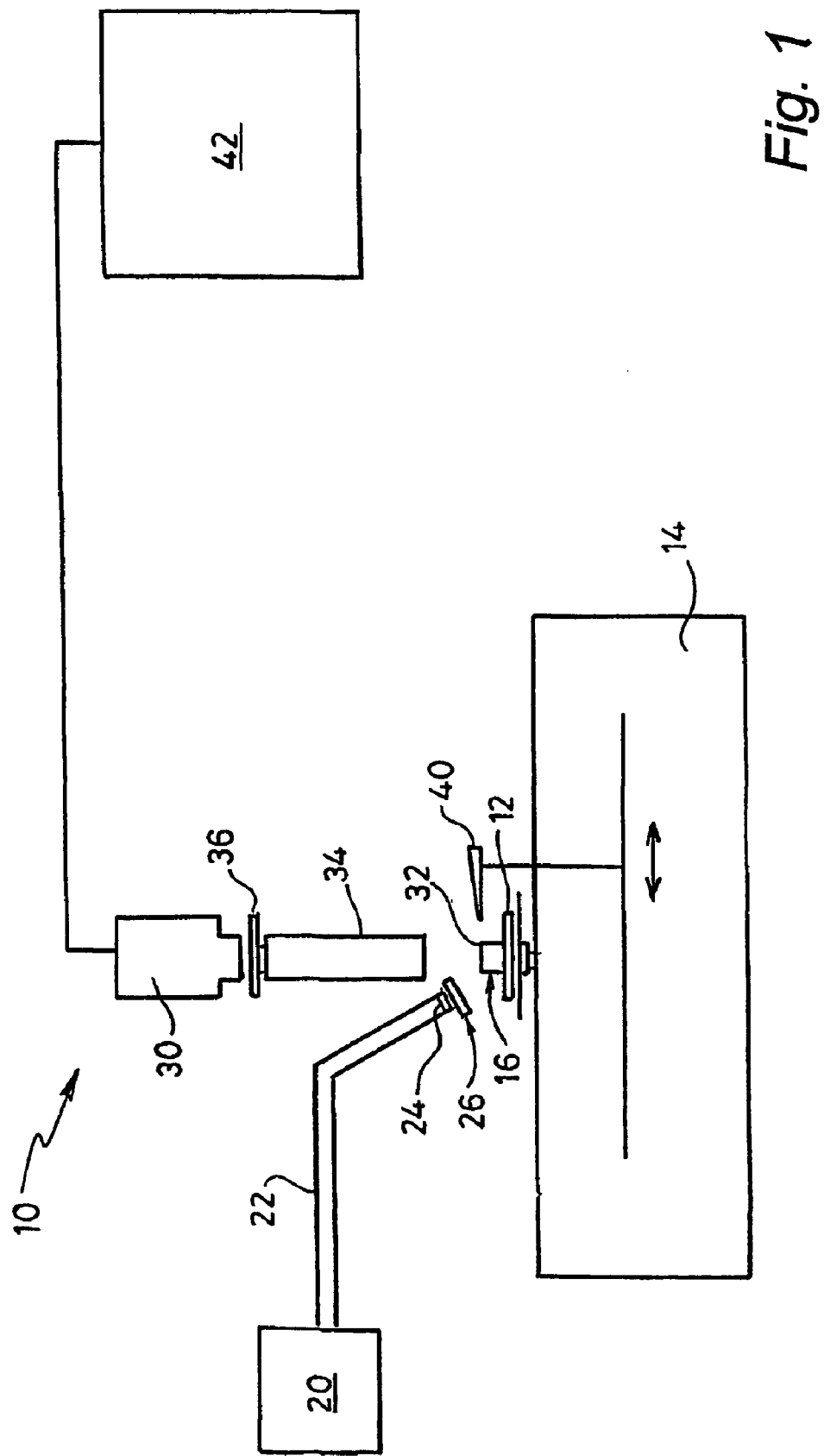
FIG. 1 shows a schematic diagram of one embodiment of apparatus in accordance with the present invention.

FIG. 1 illustrates apparatus 10 used for stimulating and analysing autofluorescence within a histological sample and which uses episcopic illumination and imaging by a CCD camera to view a surface of the sample. A mounting stage 12 of a sliding blade manual microtome 14 carries a sample 16 embedded in a wax mixture and an upper surface of the sample is illuminated by monochrome electromagnetic radiation of wavelength in the range 400–750 nm emitted by two microscope lamps 20, typically Scott KL2500 lamps. The radiation output of the lamps is directed along a wide fibre optic cable 22 with a focussing lens 24 at its output end and an excitation filter 26 of 470 nm placed between the lens 24 and the sample 16. In this way, a bright field source is adapted to produce sufficient intensity of radiation to stimulate autofluorescence in the sample 16, and the radiation can be readily directed onto the sample using the adjustable fibre optic cable 22.

A CCD camera 30, such as Princeton Instruments "CoolSnap" camera, is positioned directly above an upper face 32 of the sample, with a Monozoom microscope 34 disposed between the camera and the surface of the sample. The Monozoom microscope has a very long working distance and is adjusted so that the camera input views a clear focussed image of the sample face. An emission filter 36 of 510 nm is placed between the camera input and the microscope, so that the camera 30 receives filtered radiation at the dominant wavelength of radiation emitted as a result of autofluorescence of the sample. A blade 40 mounted on the microtome is placed in proximity to the sample 16, so as to be able to slice away successive layers of the sample after imaging.

The CCD camera 30 acquires a digital image of the sample surface by acquiring data in the usual way using a simple data capture software package (RS Image) run by a computer 42. The camera used is a relatively cheap, high resolution colour CCD device (1392×1040 pixels) and camera data is captured via a CoolSnap graphics PCI card as a 12 bit colour image. The resolution of the digital images is around 2 $\mu m^2$/pixel, although this can be increased.

The sample is prepared in a manner already known for histological samples although the preparation process uses a novel embedding medium. When embedding the sample, one needs to replace water in the sample tissue with wax. Initially the sample is exposed to increasing percentages of alcohol until gradually all water is replaced with 100% alcohol. Thus typically the sample will be placed within 70% ethanol, then 90% ethanol and lastly 100% ethanol. The alcohol is then gradually replaced with an organic chemical, such as Toluol or Histoclear, which is miscible with alcohol and wax. After this stage, the chemical is then replaced with molten wax to produce a sample where all the original water within the tissue is replaced with wax. Lastly the sample is placed in a mould and more wax added so as to provide a sample 16 where the sample tissue is infiltrated with wax and the sample is held within wax.

The particular wax embedding medium chosen for use in the present invention consists of a mixture comprising Vybar (40–80%), paraffin wax (16–57%), and stearic acid (3–4%) containing red aniline wax dye (0.1–0.35%), as supplied from Candlemakers Supplies, London. This range of compositions produces a much stiffer embedding wax than is usual and allows the embedded sample to be thinly sliced at around a thickness of 1–2 $\mu m$, as compared to a slicing thickness of 6–10 $\mu m$ for samples embedded in normal wax preparations. The red aniline wax dye is a liquid dye which supresses autofluorescence from below the top surface of the sample.

In use, the upper surface of the embedded sample is illuminated by radiation of wavelength 470 nm which stimulates autofluorescence within a top layer of the sample of less than 1 $\mu m$ thick. The sample surface emits radiation as a result of the autofluorescence, and this emitted radiation signal is detected by the CCD camera, which forms a digital image of the radiation over the sample surface. The radiation emitted by the sample varies over the surface depending on the tissue structure and thus by stimulating autofluorescence in the uppermost face 32 of the sample, an image of features within an upper thin layer of around 2 $\mu m$ is obtained by the CCD camera 30. An intrinsic property of the sample is thus used to obtain information about the sample without the need for the sample to be stained.

The autofluorescence is a very weak signal, and by carefully selecting the stimulating wavelength and the wavelength received by the CCD camera, a very clear image of features in the sample is obtained. The longer that the CCD camera is exposed to the face of the sample, the greater clarity the image has as more digital images can be obtained. By exposing the camera to the sample face for an extended period of several second, typically 4–6 seconds, and taking very large data sets using the CCD camera, very clear representations of the sample surface to a high resolution are obtained using autofluorescence. Typically 300–400 digital images are generated per hour. The required size of any data set is dependent on the sample being studied and is directly related to the sample thickness and the thickness of the cut slices. For mouse embryos, a data set of 1000 images acquired over around three hours is sufficient to visualise an entire 16 day old embryo heart, when slicing in 2 $\mu m$ sections. To image the entire embryo at the same stage, the data set can be as large as 6000 images. Thus with a digital image of approximately 5 megabytes in size, a complete data set for an embryonic heart is about 5 gigabytes in size. The degree of resolution obtained using detection of autofluorescence by the CCD camera is such that one can use the raw data from the camera as the sample image. However if desired, enhancing and filtering steps can be carried out, and if appropriate 3-D models of the samples generated.

Thus this form of imaging uses the intrinsic background property of autofluorescence which exists in any sample to view all features in the sample. This differs from known fluorescence imaging where fluorescent markers are added to the sample in some way to highlight certain features.

Once the CCD camera has been exposed for a sufficient period of time, typically 1 to 7 s, to an upper surface of the sample, the blade 40 is moved across to slice the sample at the chosen depth (usually 2 μm), and a slice of sample of the same thickness is removed. The camera then acquires image data for the next face of the sample. This process is repeated, slice by slice, until all the sample has been imaged as a series of layers. A three-dimensional reconstruction of the sample to a high degree of resolution is then possible.

In previous episcopic imaging procedures, staining has been required to show features within the sample. However it is not possible to limit penetration of the stain to less than about 6 μm depth and thus structures within the sample can only be resolved to this limit. In contrast by using autofluorescence images as with the present invention, sections of thickness 2 μm and 1 μm can be analysed as autofluorescent radiation is only emitted from this depth. Thus using autofluorescence allows more detail to be viewed in each slice, and a much improved resolution of features within the sample.

A correlation between the level of autofluorescence signal and the tissue density in the sample has been observed with denser tissue producing a more intense signal.

The detection of autofluorescence can also be combined with surface staining of the sample so as to obtain different types of information about the sample. For example, specific regions of the sample can be stained to detect the presence of beta-galactosidase enzyme activity (a bacterial enzyme which has been introduced into the mouse genome by transgenesis and is expressed in only a subset of mouse tissues). By stimulating and detecting autofluorescence, high resolution images of all the mouse tissues are obtained, with the staining allowing specific beta-galactosidase activity from the same data set also to be detected. Thus specific staining patterns of particular cells or tissues are obtained in addition to an image of the overall histological structure.

Figure 2:
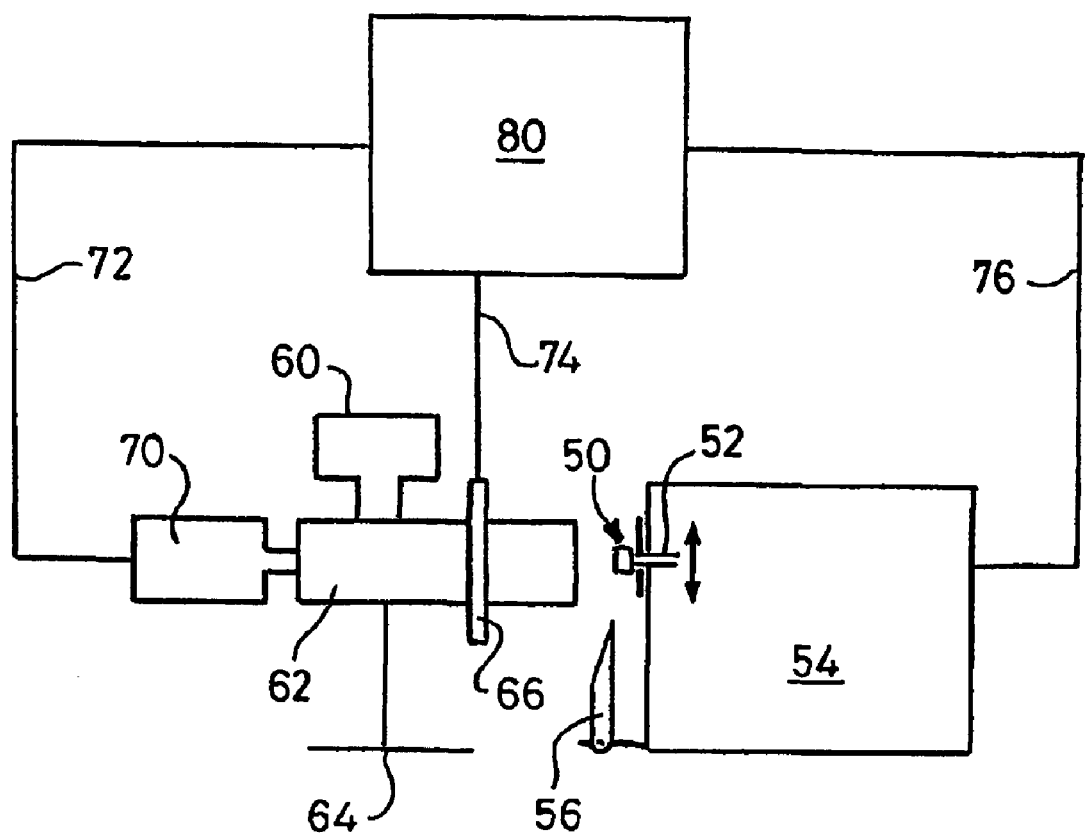
FIG. 2 shows a schematic diagram of a further embodiment comprising an automated system.

The arrangement of apparatus shown in FIG. 1 using a sliding blade manual microtome 14 in combination with a Monozoom lens 34 is not particularly suited for automation. FIG. 2 shows a further embodiment of the present invention in which the imaging process and analysis is automated. In this automated set-up, a sample block 50 is placed on a moveable mounting stage 52 of a rotary, fixed blade microtome 54 so that the sample can be moved to a rotary fixed blade 56 for sectioning. The sample 50 is illuminated by a light source 60 directed to the block surface through the optical path of a microscope 62 supported on a stand 64 and which has a filter wheel 66 containing filter sets of corresponding excitation and emission filters disposed between itself and the sample 50. As with FIG. 1, a CCD camera 70 is placed at the uppermost end of the microscope 62 and computer connections 72, 74, 76 to the camera, filter wheel and microtome are provided. Once the sample is mounted on the stage, the microscope aligned, the relevant filter sets chosen and parameters like exposure time etc specified on computer 80, the computer co-ordinates movement of the block 50 mounted on the microtome 54, sectioning of the sample, and image capturing of each sample face by the camera 70.

Figure 3:
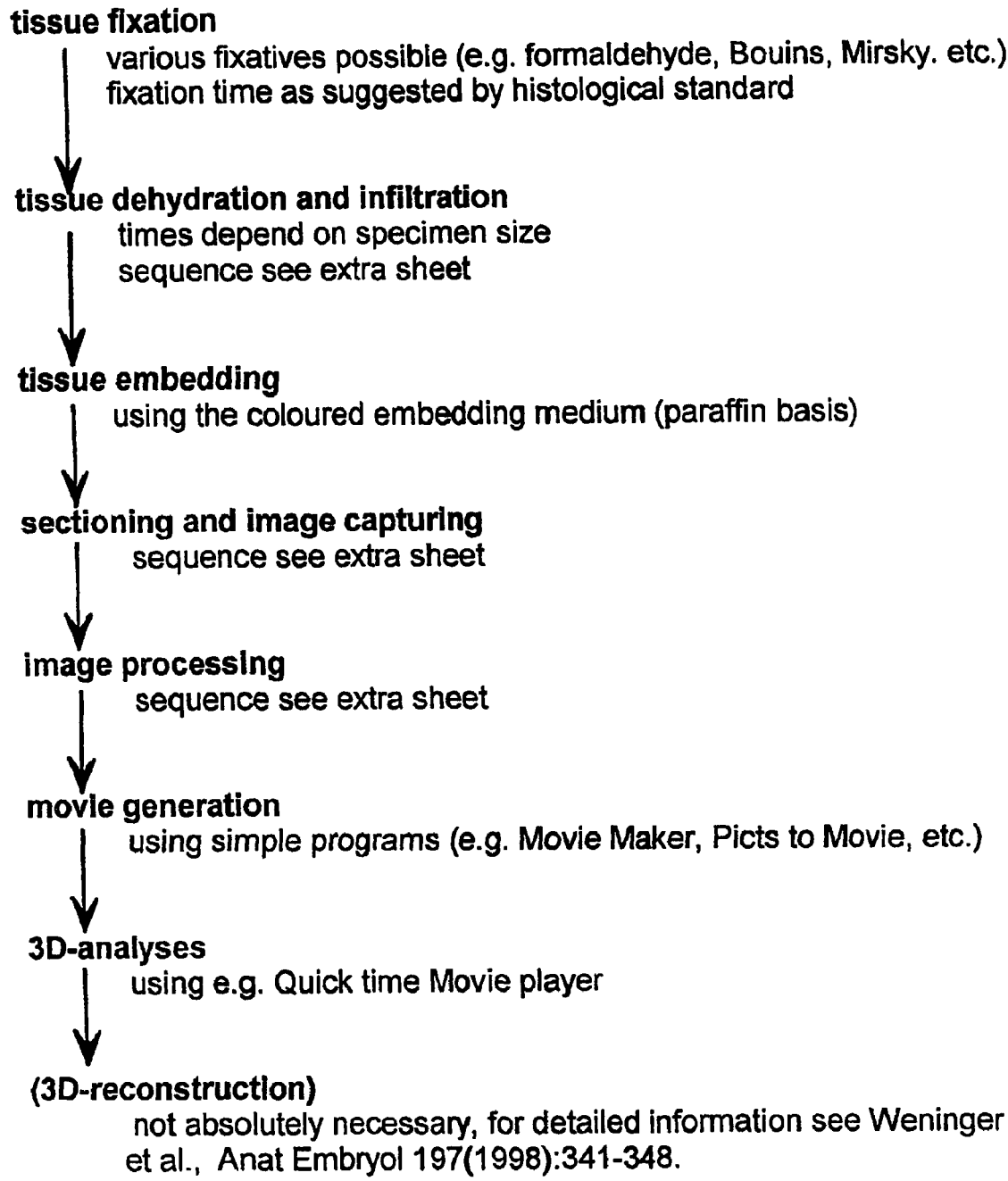
FIG. 3 is a flow diagram of procedural steps undertaken when imaging histological samples, including sectioning, image capturing and image processing.
Figure 4:
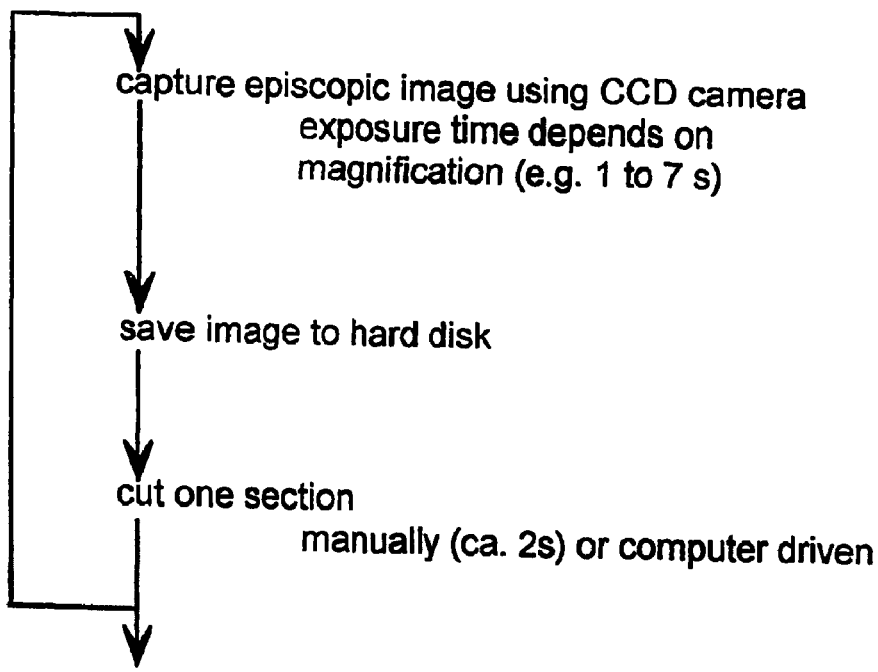
FIG. 4 is a flow diagram of steps undertaken during sectioning and image capturing.
Figure 5:
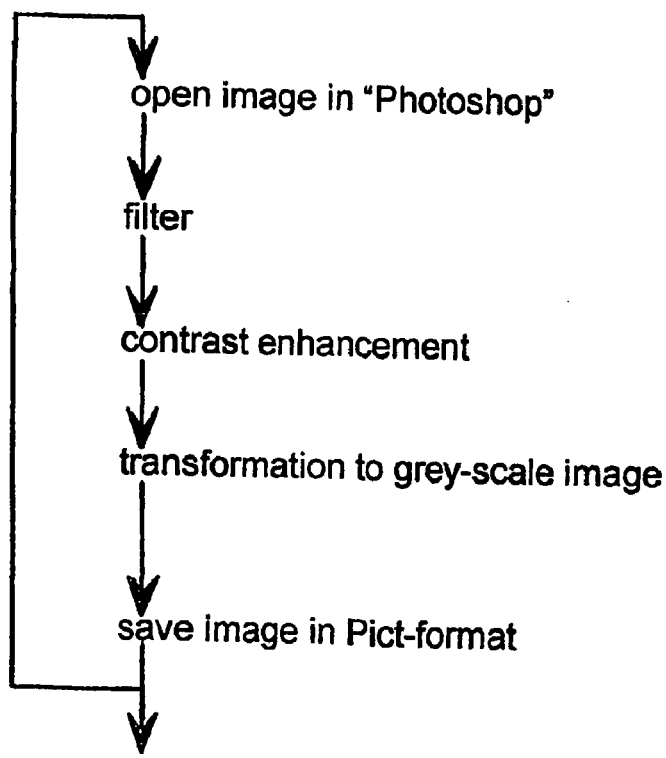
FIG. 5 is a flow diagram showing steps undertaken during image processing.

The data obtained by the CCD camera is analysed in ways common to most images obtained using CCD cameras. FIG. 3 shows the various steps used to obtain images from a histological sample and FIG. 4 shows a flow diagram illustrating how sectioning and imaging capturing is undertaken, FIG. 5 shows a flow diagram illustrating how image processing is undertaken using Adobe Photoshop (batch function).

Figure 6:
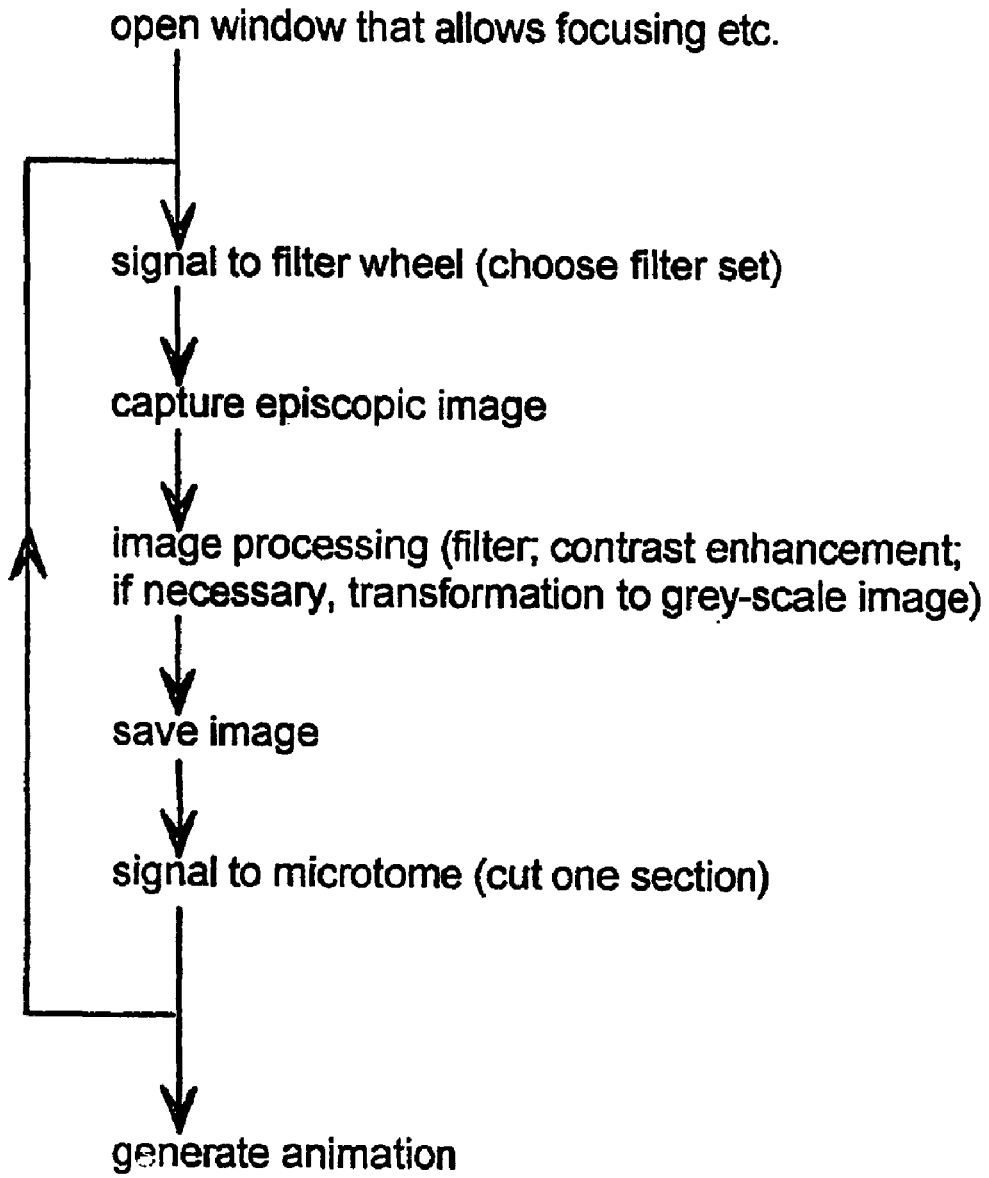
FIG. 6 is a flow diagram showing steps undertaken during imaging using the automated system.

FIG. 6 shows a flow diagram illustrating control of the automated device of FIG. 2 to obtain autofluorescence images of the sample.

The method and apparatus disclosed herein is particularly suitable for accurate analysis of tissue, organ or embryo morphology and can be used for rapid routine screenings of the phenotype of genetically modified embryos, foetuses and neonates. The method also allows detection of spatially specific staining patterns within embryo or tissue sample, revealing for example gene expression or protein expression patterns by analysing whole mount stained samples. Routine pathological analysis of tissue samples is also possible.

What is claimed is:

1. A method of imaging a histological sample comprising stimulating autofluorescence in a sample and detecting autofluorescence in the sample, wherein the sample is embedded in a wax medium with stearic acid of around 3 weight per cent, the wax medium incorporating a dye to suppress autofluorescence from below an upper surface of the sample, thereby to image features within the sample.

2. A method according to claim 1, further comprising stimulating autofluorescence by illuminating the sample with electromagnetic radiation of wavelength in the range 400750 nm.

3. A method according to claim 2, further comprising producing electromagnetic radiation by using an excitation filter of 470 nm wavelength in combination with a broadband electromagnetic radiation source.

4. A method according to claim 1, comprising recording data relating to autofluorescence in a sample for subsequent analysis and manipulation to provide information on features within a sample.

5. A method according to claim 1, further comprising staining the sample, thereby to allow detection of specific staining patterns of particular cells or tissues within the sample in combination with obtaining an image of overall histological structure through detecting autofluorescence.

6. A method according to claim 1, comprising detecting autofluorescence from an upper face of the sample, removing an upper layer of the sample and imaging a next face of the sample, and repeating these steps thereby to obtain information on autofluorescence throughout the sample.

7. A wax embedding medium for use in embedding histological samples, the medium comprising stearic acid of around 3 weight per cent and incorporating a dye to suppress autofluorescence from below an upper surface of a sample.

8. A wax embedding medium according to claim 7, wherein the dye is red aniline wax dye.

* * * * *